US009539357B2

(12) United States Patent
Ashraf et al.

(10) Patent No.: US 9,539,357 B2
(45) Date of Patent: Jan. 10, 2017

(54) NONWOVEN WEB MATERIAL INCLUDING FIBERS FORMED OF RECYCLED POLYESTER, AND METHODS FOR PRODUCING

(71) Applicant: The Procter & Gamble Company, Cincinnati, OH (US)

(72) Inventors: Arman Ashraf, Mason, OH (US); Ronald Thomas Gorley, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 14/069,809

(22) Filed: Nov. 1, 2013

(65) Prior Publication Data

US 2015/0126949 A1    May 7, 2015

(51) Int. Cl.
A61F 13/15      (2006.01)
A61L 15/22      (2006.01)
D04H 1/4274     (2012.01)
D04H 3/007      (2012.01)
D04H 3/011      (2012.01)
D04H 3/016      (2012.01)
D04H 3/147      (2012.01)
(Continued)

(52) U.S. Cl.
CPC ........ *A61L 15/225* (2013.01); *A61F 13/15617* (2013.01); *D01F 8/06* (2013.01); *D01F 8/14* (2013.01); *D04H 1/4274* (2013.01); *D04H 3/007* (2013.01); *D04H 3/011* (2013.01); *D04H 3/016* (2013.01); *D04H 3/147* (2013.01); *D04H 3/153* (2013.01); *D04H 3/16* (2013.01); *D04H 3/005* (2013.01); *Y10T 442/637* (2015.04); *Y10T 442/638* (2015.04); *Y10T 442/681* (2015.04)

(58) Field of Classification Search
CPC ... A61F 13/15617; D04H 3/007; D04H 3/011; D04H 3/016; D01F 8/06
USPC .......................... 604/367, 370, 372, 365, 366
See application file for complete search history.

(56) References Cited

U.S. PATENT DOCUMENTS

| 3,860,003 A | 1/1975 | Buell |
| 4,940,464 A | 7/1990 | Van Gompel et al. |

(Continued)

FOREIGN PATENT DOCUMENTS

| CN | 102995400 A | 3/2013 |
| JP | 2007-197857 A | 8/2007 |

(Continued)

OTHER PUBLICATIONS

U.S. Appl. No. 13/538,140, filed Jun. 29, 2012, Ashraf et al.

(Continued)

*Primary Examiner* — Jacqueline Stephens
(74) *Attorney, Agent, or Firm* — William E. Gallagher

(57) ABSTRACT

A nonwoven web material including fibers formed of a polyolefin and a polyester is disclosed. The fibers may include fine fibers produced by, for example, a meltblowing process. The polyolefin may be polypropylene and the polyester may be polylactic acid. The polylactic acid may be obtained and included by recycling scrap nonwoven material containing a polylactic acid component, hydrolyzing the polylactic acid component to reduce its viscosity, blending the hydrolyzed polylactic acid with a polyolefin resin, and melt-spinning the blended material to form fibers. A related process is disclosed.

21 Claims, 4 Drawing Sheets

(51) Int. Cl.
*D04H 3/153* (2012.01)
*D04H 3/16* (2006.01)
*D01F 8/06* (2006.01)
*D01F 8/14* (2006.01)
*D04H 3/005* (2012.01)

(56) References Cited

U.S. PATENT DOCUMENTS

| | | |
|---|---|---|
| 5,037,416 A | 8/1991 | Allen et al. |
| 5,092,861 A | 3/1992 | Nomura et al. |
| 5,151,092 A | 9/1992 | Buell et al. |
| 5,246,433 A | 9/1993 | Hasse et al. |
| 5,269,775 A | 12/1993 | Freeland et al. |
| 5,554,145 A | 9/1996 | Roe et al. |
| 5,569,234 A | 10/1996 | Buell et al. |
| 5,571,096 A | 11/1996 | Dobrin et al. |
| 5,897,545 A | 4/1999 | Beckman et al. |
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,506,873 B1 | 1/2003 | Ryan et al. |
| 6,524,981 B1 | 2/2003 | Srinivasan |
| 2003/0176136 A1* | 9/2003 | Wadsworth ....... A61F 13/15252 442/401 |
| 2003/0233082 A1 | 12/2003 | Beckman et al. |
| 2004/0102123 A1 | 5/2004 | Bowen |
| 2004/0162536 A1 | 8/2004 | Becker et al. |
| 2004/0167486 A1 | 8/2004 | Becker et al. |
| 2008/0287026 A1* | 11/2008 | Chakravarty et al. ........ 442/414 |
| 2008/0312617 A1 | 12/2008 | Hundorf et al. |
| 2009/0048403 A1 | 2/2009 | Costantini et al. |
| 2010/0004362 A1 | 1/2010 | Ikegame et al. |
| 2010/0048082 A1* | 2/2010 | Topolkaraev ..... A61F 13/15252 442/400 |
| 2010/0222755 A1 | 9/2010 | Westwooe |
| 2011/0189915 A1 | 8/2011 | Monimoto et al. |
| 2011/0196325 A1 | 8/2011 | Isele et al. |
| 2011/0244257 A1 | 10/2011 | Paulino et al. |
| 2012/0046411 A1 | 2/2012 | Kulshrestha et al. |
| 2012/0051672 A1 | 3/2012 | Foss et al. |
| 2012/0315225 A1 | 12/2012 | Porbeni et al. |
| 2012/0315816 A1 | 12/2012 | Fowler et al. |
| 2013/0052901 A1* | 2/2013 | Bond et al. ................... 442/327 |
| 2015/0123304 A1 | 5/2015 | Ashraf et al. |

FOREIGN PATENT DOCUMENTS

| | | |
|---|---|---|
| JP | 2013-023805 A | 2/2013 |
| WO | WO 95-16746 | 6/1995 |
| WO | WO 2009-060384 | 5/2009 |
| WO | WO 2009-151437 | 12/2009 |
| WO | WO 2011-073265 A1 | 6/2011 |

OTHER PUBLICATIONS

PCT International Search Report, mailed Mar. 5, 2015 (12 pages).
All Office Actions and Responses in U.S. Appl. No. 14/069,843, Arman Ashraf et al., filed Nov. 1, 2013.

* cited by examiner

NONWOVEN WEB MATERIAL INCLUDING FIBERS FORMED OF RECYCLED POLYESTER, AND METHODS FOR PRODUCING

BACKGROUND OF THE INVENTION

Traditionally, nonwoven webs used as components of disposable absorbent articles have been formed of fibers spun from polymer resins, frequently resins including polyolefins such as polypropylene. While such resins may be used to form fibers that are flexible and smooth and have a soft tactile feel and desirable mechanical properties, they are derived from petroleum. In recent years, demand has developed for alternative materials that are more quickly biodegradable and/or are derived from resources deemed to be renewable.

One such material that is currently receiving interest as an alternative is polylactic acid (PLA). PLA is a thermoplastic aliphatic polyester derived from resources such as corn starch or sugarcane. It has been found that fibers spun from PLA generally exhibit less elongation at break and significantly greater modulus than fibers of comparable size or denier spun from polyolefins such as polypropylene.

It is possible to manufacture a nonwoven web from fibers spun entirely from PLA resin. While the comparatively greater modulus of PLA fibers may impart comparatively greater tensile strength to a nonwoven web formed of them, fibers formed of currently available PLA resins tend to be comparatively less flexible and have a rough tactile feel. Thus, a nonwoven web formed of entirely PLA fibers may be more stiff and rough-feeling, as compared with a nonwoven web formed of polyolefin (e.g., polypropylene) fibers of similar size/denier and basis weight. This may make a PLA fiber nonwoven web undesirable for applications in which flexibility, tactile softness and smoothness are desirable, such as, for example, to form components of wearable absorbent articles such as disposable diapers, absorbent pants, feminine hygiene pads and other articles. In such articles, tactile softness may be desired because nonwoven web components often contact (and sometimes rub) the skin; and tactile softness and flexibility may be desired for wearer comfort.

It has been further found, however, that core-sheath configuration bicomponent fibers may be spun using PLA to form the core section and a polyolefin (e.g. polypropylene) to form the sheath section. The polyolefin sheath section can give the fiber tactile surface feel characteristic of all-polyolefin fibers, while the PLA core section can maintain or even enhance fiber tensile strength, and replaces a portion of the petroleum-derived component with a component derived from resources deemed to be renewable.

In any process involving the production of polymer fiber nonwoven web or the production of articles in which the nonwoven web is used as a component, there will be an associated production of scrap such as edge trimming scrap, cutoff scrap, material that is not useable or not saleable because it does not meet specifications, etc. It is typical for such scrap to be recycled into the spinning process to help reduce the production of waste, and help control material costs. A nonwoven web containing polyolefin and PLA components together, however, presents technical complications for recycling because polyolefin and PLA are generally immiscible with each other, and thus, tend to form separate phases in melt. If spinning a melted blend of these resins is attempted, problems may be presented including inconsistently shaped fibers, weakened or broken fibers, resin accumulation and "drip" at the spinnerets, and others that may deleteriously affect web quality, consistency and mechanical properties.

Accordingly, there is a need for ways in which materials including combinations of PLA and polyolefins such as polypropylene can be successfully recycled in a fiber spinning/nonwoven web manufacturing operation.

DETAILED DESCRIPTION OF THE INVENTION

Definitions

Figure 1:
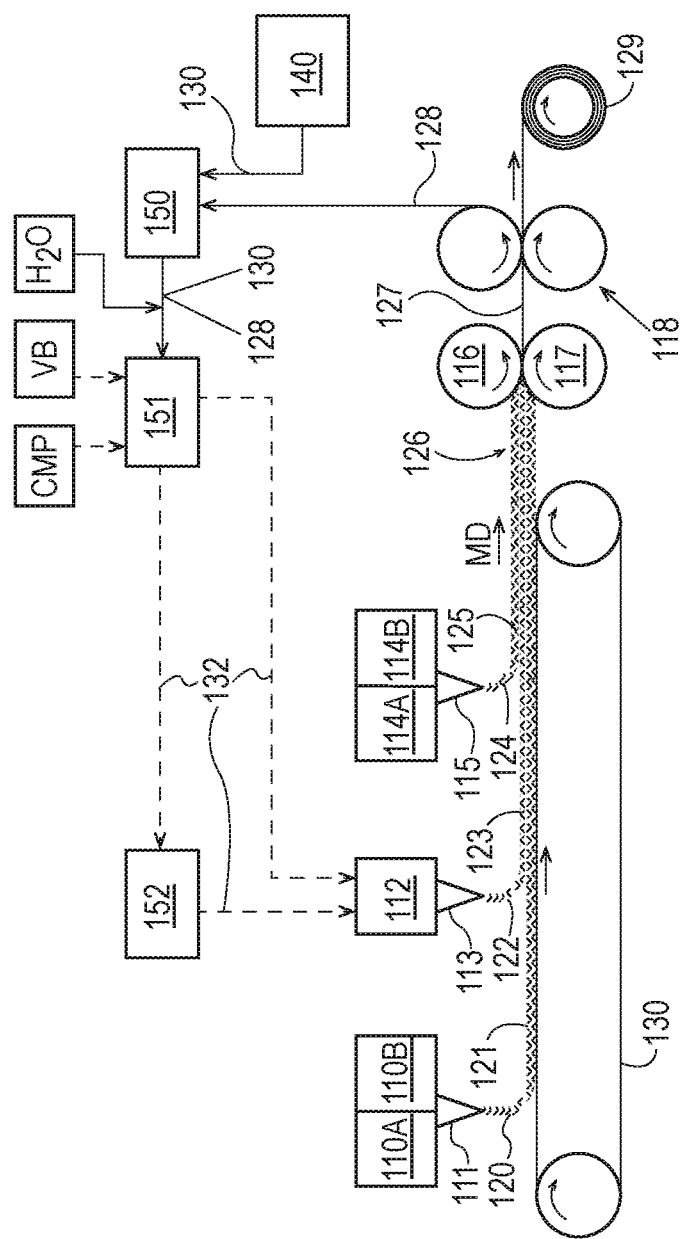
FIG. 1 is a schematic side-view depiction of a system and process for producing a nonwoven which includes recycling of trim or scrap material.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments and pads, feminine hygiene products, breast pads, care mats, bibs, wound dressing products, and the like. As used herein, the term "exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article. The absorbent core may also include a cover layer or envelope. The cover layer or envelope may comprise a nonwoven. In some examples, the absorbent core may include one or more substrates, an absorbent polymer material, and a thermoplastic adhesive material/composition adhering and immobilizing the absorbent polymer material to a substrate, and optionally a cover layer or envelope.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein the first substrate and second substrate are separated by a multiplicity of superabsorbent particles. There may be some extraneous superabsorbent particles outside of this area between the first substrate 64 and second substrate.

"Airfelt" is used herein to refer to comminuted wood pulp, which is a form of cellulosic fiber.

"Bicomponent" refers to fiber having a cross-section comprising two discrete polymer components, two discrete blends of polymer components, or one discrete polymer component and one discrete blend of polymer components. "Bicomponent fiber" is encompassed within the term "Multicomponent fiber." A Bicomponent fiber may have an overall cross section divided into two or more subsections of the differing components of any shape or arrangement, including, for example, coaxial subsections, core-and-sheath subsections, side-by-side subsections, radial subsections, etc.

"Cross direction"—with respect to a web material, refers to the direction along the web material substantially perpendicular to the direction of forward travel of the web material through the manufacturing line in which the web material is manufactured.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pant" which is defined below.

"Fiber" and "filament" are used interchangeably.

"Film"—means a skin-like or membrane-like layer of material formed of one or more polymers, which does not have a form consisting predominately of a web-like structure of consolidated polymer fibers and/or other fibers.

"Length" or a form thereof, with respect to a diaper or training pant, refers to a dimension measured along a direction perpendicular to the waist edges and/or parallel to the longitudinal axis.

"Machine direction"—with respect to a web material, refers to the direction along the web material substantially parallel to the direction of forward travel of the web material through the manufacturing line in which the web material is manufactured.

"Monocomponent" refers to fiber formed of a single polymer component or single blend of polymer components, as distinguished from Bicomponent or Multicomponent fiber.

"Multicomponent" refers to fiber having a cross-section comprising more than one discrete polymer component, more than one discrete blend of polymer components, or at least one discrete polymer component and at least one discrete blend of polymer components.

"Multicomponent fiber" includes, but is not limited to, "Bicomponent fiber." A Multicomponent fiber may have an overall cross section divided into subsections of the differing components of any shape or arrangement, including, for example, coaxial subsections, core-and-sheath subsections, side-by-side subsections, radial subsections, etc.

A "nonwoven" is a manufactured sheet or web of directionally or randomly oriented fibers, consolidated and bonded together by friction, cohesion, adhesion or one or more patterns of bonds and bond impressions created through localized compression and/or application of heat or heating energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Tensile Strength" refers to the maximum tensile force (Peak Force) a material will sustain before tensile failure.

"Width" or a form thereof, with respect to a diaper or training pant, refers to a dimension measured along a direction parallel to the waist edges and/or perpendicular to the longitudinal axis.

"Z-direction," with respect to a web, means generally orthogonal or perpendicular to the plane approximated by the web in the machine and cross direction dimensions.

Processes for continuous and discontinuous fiber spinning of molten polymer materials, typically thermoplastics, are commonly referred to as spunmelt processes. Spunmelt processes may include both meltblowing processes and spunbond processes. A spunbond process includes supplying a molten polymer, extruding it under pressure through a large number of orifices in a plate known as a spinneret or die. The resulting continuous fibers are quenched and drawn by any of a number of methods and systems, such as by slot draw systems, attenuator guns, or Godet rolls, for example. In the spunlaying or spunbonding process, the continuous fibers are collected as a loose web upon a moving foraminous surface, such as a wire mesh conveyor belt, for example. When more than one spinneret is used in line for forming a multi-layered web, the subsequent nonwoven component layers are collected upon the uppermost surface of the previously formed nonwoven component layer.

The meltblowing process is similar to the spunbonding process for forming a layer of a nonwoven material, wherein a molten polymer is extruded under pressure through orifices in a spinneret or a die. Distinguishing the meltblowing process from the spunbond/spunlaid process, as streams of polymer exit the spinnerets, they are subjected to a high velocity gas (e.g., air) flow, such that the moving gas (which may be heated) impinges on the fibers and attenuates them. The attenuation substantially reduces the diameters of the fibers and also tends to break them into shortened random lengths so that fine fibers of indeterminate, varying lengths are produced. This differs from the spunbonding process where continuity of the fibers is substantially preserved. Often, meltblown nonwoven structures are layered with spunbond nonwoven structures to form spunbond, meltblown ("SM") webs or spunbond, meltblown, spunbond ("SMS") webs, which can be formed as suitably strong webs with liquid barrier properties imparted by the meltblown layers.

FIG. 1 schematically depicts a system and process for producing a nonwoven web material including polyolefin and PLA components, in which trim or scrap material may be recycled.

The nonwoven web may be produced by compressing and bonding two, three or more layers of fibers spun and deposited onto a moving surface (such as a conveyor belt). At least one, or more preferably both, of the outermost layers may be formed of spunbond fibers. (As depicted in FIG. 1, the outer layers would be the lowermost and uppermost layers, deposited first and last in order, respectively).

First and second melt extruders 110A and 110B, respectively, may be used to melt and drive a combination of polymer resins into a beam of first spinnerets 111. Extruder 110A may be configured to melt and drive a first polymer resin and extruder 110B may be configured to melt and drive a second polymer resin differing from the first. First spinnerets 111 may be configured as multicomponent, e.g., bicomponent fiber spinnerets, wherein they receive separate pressurized streams of the differing melted resins and form them into single fibers having two distinct longitudinal component sections. Multicomponent, e.g., bicomponent (sometimes called "crimped" and/or "conjugated"), fibers and processes for spinning them are known and described in, for example, copending U.S. patent application Ser. No. 13/538,140 and U.S. Pat. App. Pub. No. 2011/0189915, which are incorporated fully herein by reference to the extent not inconsistent herewith. Bicomponent fiber spinnerets may be selected with varying configurations that produce bicomponent fibers having, for example, side-by-side, core/sheath, "islands in the sea," segmented pie, etc., component configurations.

For example, spunbond spinnerets 111 may be configured to produce bicomponent fibers of a core-sheath configuration, wherein the core of the fiber is formed of a first polymer and the sheath of the fiber is formed of a second polymer. More particularly, the first polymer used to form the core section may be a PLA, and a second polymer used to form the sheath section may be a polyolefin, e.g., polypropylene. Although these two polymers are generally immiscible with each other when melted, the core/sheath arrangement ensures that the longitudinal component sections of the spun fibers do not separate when cooled because the sheath section surrounds and contains the core section. Thus, spinnerets 111 may be configured as core/sheath bicomponent spunbond spinnerets that form core/sheath bicomponent first fibers 120 in a spunlaid/spunbond process, in which first fibers 120 accumulate to form a first deposited layer 121 of bicomponent fibers on a moving conveyor belt 130.

A third extruder 112 and associated beam of second spinnerets 113 may be included to melt a third polymer resin and form second fibers 122, which accumulate to form a second deposited layer 123 of fibers overlaying the first deposited layer 121. Spinnerets 113 may be monocomponent fiber spinnerets configured to produce monocomponent fibers.

At least one of the inner layers may be formed of meltblown fibers or other fine fibers. (For purposes herein, "fine fibers" means fibers having an average diameter of 0.10 μm to 10 μm.) Since this diameter range is generally much smaller than that of spunbond fibers, a layer of fine fibers will have a comparatively much greater number and numerical density of fibers than a layer of spunbond fibers of the same basis weight. This results in a comparatively smaller pore size in the web, such that the fine fiber layer may impart opacity as well as resistance to passage of liquids and/or adhesives through the web, and in some circumstances, may render the web effectively liquid impermeable. At the same time, the fine fiber layer and thus the web may ordinarily be air and vapor permeable. This may make the web especially useful in applications in which a combination of effective liquid impermeability combined with vapor permeability are desired. Such applications may include use of the web to form diaper components such as barrier cuffs, core covers and backsheets. For example, see U.S. application Ser. No. 13/024,826, which is incorporated fully herein by reference to the extent not inconsistent herewith. While a fine fiber layer of a web may impart qualities such as liquid impermeability and opacity, it may lack tensile strength typically needed for processing. As noted, however, one or more spunbond fiber layers may be included to impart desired tensile strength to the web, as a result of their greater fiber size.

Accordingly, additional equipment may be included to constitute a meltblowing or other fine fiber spinning system that produces fine fibers at third extruder 112 and second spinnerets 113. The fine fibers may be formed predominately of polypropylene.

Fourth and fifth extruders 114A and 114B, like first and second extruders 110A and 110B, may be included and used to melt and drive a combination of a fourth polymer resin and a fifth polymer resin into a beam of third spinnerets 115. Third spinnerets 115 also may be configured as bicomponent fiber spinnerets to produce bicomponent fibers of any suitable longitudinal section configuration, such as core/sheath, where one of the longitudinal sections is formed of the fourth polymer and the other of the longitudinal section is formed of the fifth polymer. The fourth polymer may be a PLA and used to form a core fiber section, and the fifth polymer may be a polyolefin such as polypropylene and used to form a sheath section, of third fibers 124. Third spinnerets 115 may be used to form third fibers 124 which may be accumulated to form third deposited layer 125 overlaying the second deposited layer 123, where deposited layers 121, 123 and 125 form a layer combination 126 of deposited fiber layers.

Bicomponent spunbond fibers produced at spinnerets 111 and/or 115 may have varying relative weight percent contents of first and second components. Where the component resins are selected to be PLA and a polyolefin such as polypropylene, for example, the weight percent ratio of PLA to polyolefin may be from 10:90 to 90:10. Generally, higher ratios of PLA to polyolefin will result in a comparatively stiffer fiber having greater tensile strength; where this is desired, the range of PLA to polyolefin may be selected to be from 50:50 to 90:10, or 60:40 to 90:10, or even 70:30 to 90:10. Conversely, lower ratios of PLA to polyolefin will result in a comparatively more flexible fiber; where this is desired, the range of PLA to polyolefin may be selected to be from 10:90 to 50:50, or 10:90 to 40:60, or even 10:90 to 30:70.

Layer combination 126 may then be conveyed into the nip between calender/bonding rollers 116, 117, which through pressure, and optionally, added heating energy to heat the fibers in the nip, compress and consolidate the fibers of the layer combination 126, and bond the fibers via a pattern of bonds to form a pattern-bonded nonwoven web 127. As an alternative to direct application of heat via heated calender bonding roller, ultrasonic energy may be supplied to heat the fibers, which may provide advantages in some circumstances.

As an alternative or supplement to calender bonding, following consolidation the layer combination 126 of fiber layers may be through-air bonded, adhesive bonded, hydroentangled, needlepunched, or subjected to any other process that bonds or entangles the fibers of the layers to convert the layer combination 126 to a cohesive cloth-like nonwoven web.

Following formation of nonwoven web 127, it may be passed through an edge-trimming apparatus 118 which trims off one or both of the longitudinal edges of the web on one or both sides, along the machine direction (i.e., parallel to the direction of the moving web). This process may be used to impart a uniform cross-direction width and neat machine-direction longitudinal edge(s) to the nonwoven web 127. The edge-trimming process will generate edge trim scrap 128.

Following formation of nonwoven web 127 and optionally, edge trimming, the web 127 may be accumulated on a supply roll 129, which can be stored for future use and/or transported to be used in downstream converting operations. Alternatively, web 127 may be conveyed directly to downstream converting operations without any interim accumulation. Downstream converting operations may include systems 140 and processes used in manufacturing absorbent articles such as but not limited to disposable diapers, disposable training pants, feminine hygiene pads, personal and baby cleansing wipes, and household cleaning cloths and cleaning pads in which the nonwoven web 127 is a component material. Downstream converting operations and systems 140 may also generate converting scrap 130 that includes unused or unusable portions of the nonwoven web 127 resulting from trimming, cutting, rejections of defective materials or products, etc.

Referring again to FIG. 1, where one or both of first fibers 120 and third fibers 124 are spunbond bicomponent fibers, edge trim scrap 128 and/or converting scrap 130 will contain the differing polymer components of the fibers. While it is generally desirable to recycle such scrap to reduce creation of unusable waste and to help maximize value realized from purchased materials (i.e., help control material costs), it is generally not believed economically and technically practical to attempt to separate the differing polymers from each other prior to recycling (e.g. by mechanical separation methods.)

But when the polymer components are immiscible with each other in the melted phase (for example, where the two polymer components include PLA and a polyolefin such as polypropylene), this can create problems in attempting to spin the recycled polymers into fibers. The immiscible combination of melted polymers cannot ordinarily be spun in a spunbond process without creating a risk of compromising the strength, size/shape consistency and/or length of the resulting fibers. Additionally, passing such a combination through spunbond spinnerets can result in processing problems such as polymer accumulation and "drip" at the spinnerets, in which drops of melted, unspun polymer resin form at the spinnerets and eventually are drawn or drop into the layers, comprising the consistency and quality of the nonwoven web product.

It is believed, however, that appropriate further processing steps may be employed which are economically and technically practical to enable recycling of fiber scrap, which includes PLA, into a nonwoven web manufacturing operation.

Trim scrap 128 and/or process scrap 130 may be fed into a shredder 150 which mechanically divides the scrap into small pieces.

Following shredding, trim scrap 128 and/or process scrap 130 may be fed into recycling extruder 151 together with suitable quantities of moisture ($H_2O$) to hydrolyze the PLA, which causes the molecule chains to break down into smaller units, thereby decreasing the viscosity and increasing the melt flow rate of the PLA resin component. Processes for hydrolyzing PLA are described in, for example, U.S. Pat. App. Pub. No. 2010/0048082 and PCT App. Pub. No. WO 2009/151437, the disclosures of which are incorporated herein by reference to the extent not inconsistent herewith. The quantity of the water added, measured in weight, may fall within the range of 0.01 percent to 8 percent of the weight of the PLA present.

Optionally, an effective amount of a vis-breaker (VB) may be added to the resin in the recycling extruder 151 to degrade the polyolefin polymer chains into smaller units, thereby also decreasing the polyolefin resin viscosity and increasing its melt flow rate, which may enhance downstream processibility in some circumstances. Where, for example, the polyolefin is polypropylene, a suitable vis-breaker may be IRGATEC CR 76, a polypropylene modifier available from BASF Schweiz AG, Basel, Switzerland.

Also, optionally, an effective amount of a compatibilizer (CMP) may be added to increase the miscibility of the PLA and the polyolefin. Suitable compatibilizers may include LOTADER AX8840 (melt flow rate ("MFR")=5 g/10 min), a product of Arkema Inc., King of Prussia, Pa.; ELVALOY 1224AC (MFR=2 g/10 min) and FUSABOND M603 (MFR=25 g/10 min), products of E.I. DuPont de Nemours and Company, Wilmington, Del.; and POLYBOND 3200 (MFR=115 g/10 min), a product of Chemtura Corporation, Middlebury, Conn.; and modified SEBS (styrene-ethylene/butylene-styrene) polymers such as DYNALON 8630P (MFR=15 g/10 min), a product of JSR Corporation, Tokyo, Japan; TUFTEC N503 (MFR=20 g/10 min), a product of Asahi Kasei Chemicals Corporation, Tokyo, Japan; and FG1924 (MFR=11 g/10 min), a product of Kraton Polymers LLC, Houston, Tex. An effective amount of a compatibilizer may be from 1.0 to 9.0 weight percent of the weight of the combination of PLA and polyolefin resins.

Following processing in the recycling extruder 151, the combination 132 of PLA and polyolefin resins may be fed to a pelletizer 152, which forms the melted resin combination into pellets for storage and/or transport for later use. The recycled resin pellets may then be admixed with virgin single-polymer resin in the third extruder 112, thereby supplementing the resin supply used to form fine fibers 122. Alternatively, the pelletizing step may be omitted and the melted, recycled resin combination 132 may be fed directly from the recycling extruder 151 to third extruder 112. Although the combination of melted, reduced-viscosity PLA and polyolefin resins may be unsuitable in some circumstances for use to produce fibers by spinning through spunbond spinnerets, it believed suitable for admixing with virgin resin in limited quantities for use in a meltblowing process. Without intending to be bound by theory, it is believed that, to the extent fiber length, shape consistency and/or strength may be compromised to some extent by the admixing of recycled PLA resin with the virgin polyolefin resin to form fine fibers, this does not have substantial negative consequences if the fine fibers are used to form a layer of a layer combination 126 that also includes at least one layer formed of spunbond fibers. The spunbond fibers may still be relied upon to impart desired mechanical properties to the web product. Additionally, it is believed that, to the extent inclusion of recycled PLA resin may result in the formation of frangible/splittable meltblown fibers, this may provide a further advantage of creating even finer fibers formed of split meltblown fibers, contributing to web opacity and liquid impermeability.

In another alternative, the combination 132 of PLA and polyolefin resins may be fed to one or more of other extruders 10A, 10B, 114A, 114B, with appropriately configured spinnerets and/or inclusion of a compatibilizer to aid blending of the recycled PLA and polyolefin components, to supplement virgin resin(s) fed to those extruders.

It is believed that the process described above enables the economically and technically practical recycling of scrap containing PLA and polyolefin polymer components, for the formation of a nonwoven web product having desirable properties including tensile strength, liquid impermeability, opacity, enhanced biodegradability, and use of material resources deemed to be renewable.

A nonwoven web manufactured according to the process, and having the features, described above may be used to form a component of a disposable absorbent article, including, for example, the topsheet, an outer nonwoven layer of a backsheet, barrier cuffs, side panels, etc.

Figure 2:
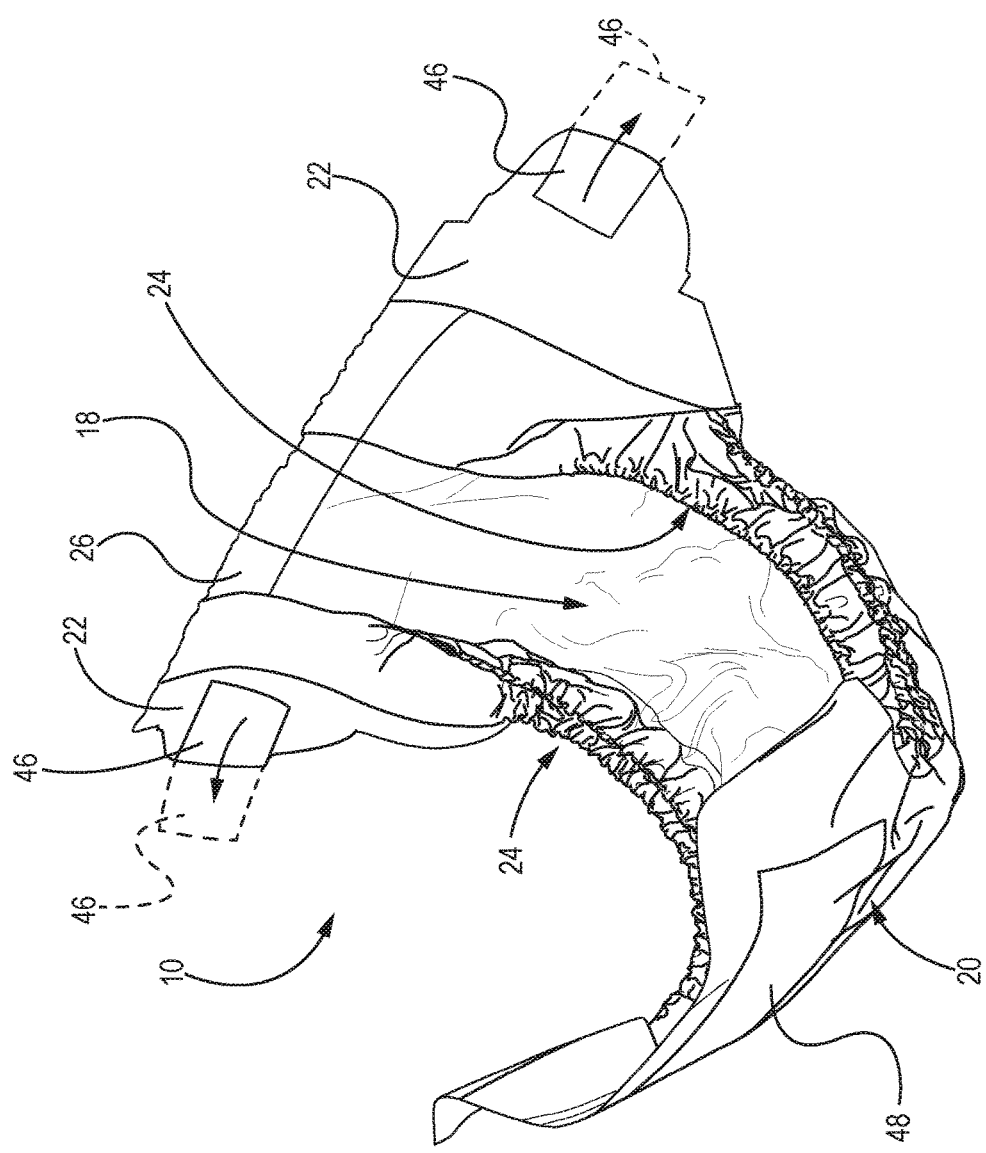
FIG. 2 is a perspective view of a disposable diaper shown laid out horizontally in a relaxed state, wearer-facing surfaces up.
Figure 3:
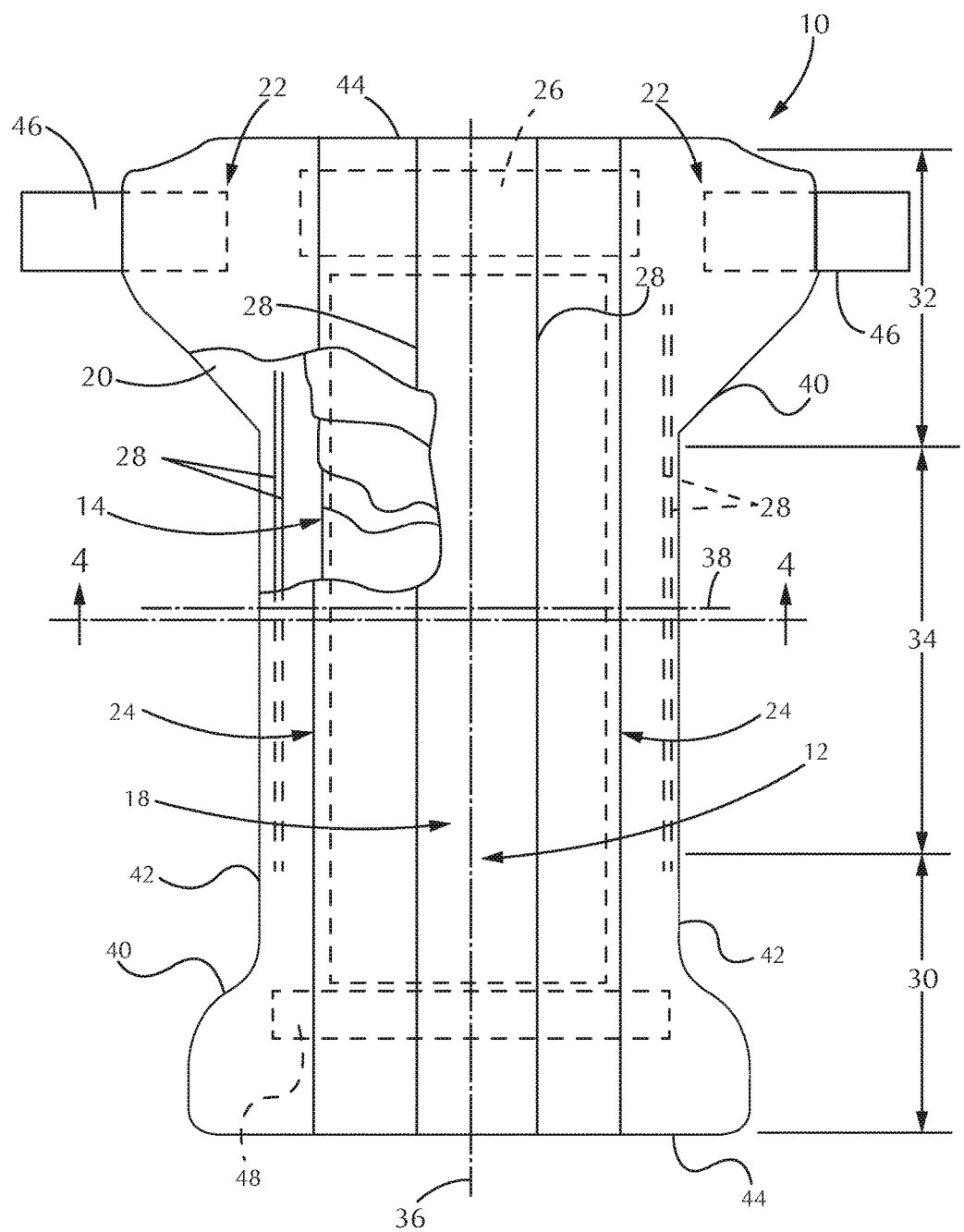
FIG. 3 is a plan view of a disposable diaper shown laid out horizontally in a stretched out, flattened state (stretched out against elastic contraction induced by the presence of elastic members), wearer-facing surfaces facing the viewer.
Figure 4:
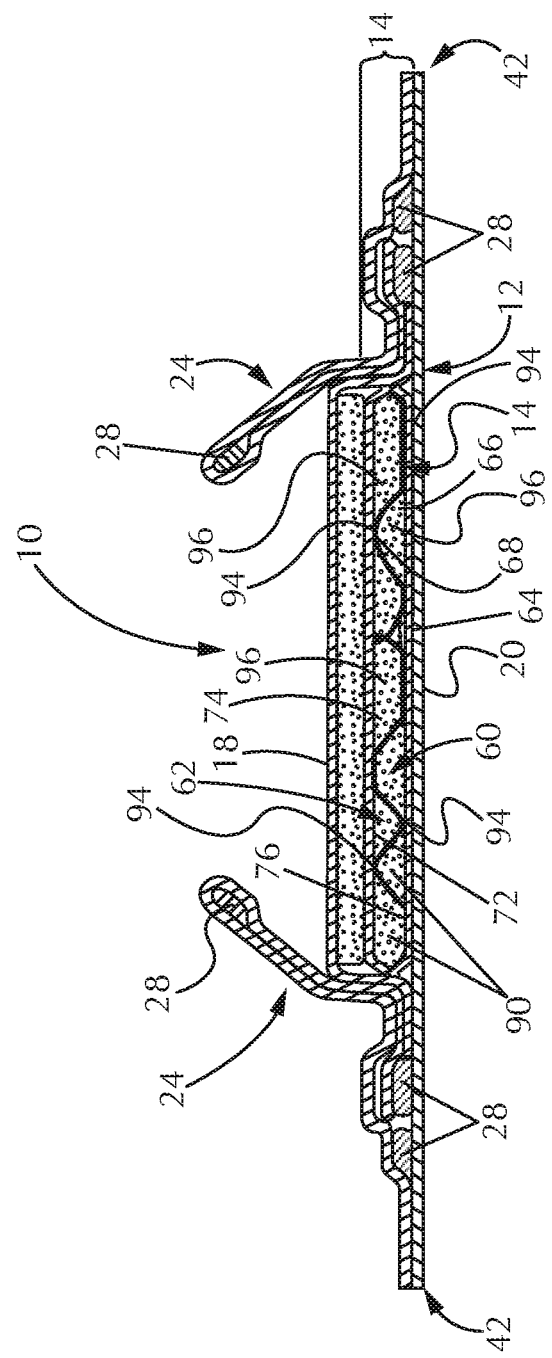
FIG. 4 is a cross section of the diaper depicted in FIG. 3, taken through line 4-4 in that figure.

FIG. 2 is a perspective view of a diaper 10 in a relaxed, laid-open position as it might appear opened and lying on a horizontal surface. FIG. 3 is a plan view of a diaper 10 shown in a flat-out, uncontracted state (i.e., without elastic induced contraction), shown with portions of the diaper 10 cut away to show underlying structure. The diaper 10 is depicted in FIG. 3 with its longitudinal axis 36 and its lateral axis 38. Portions of the diaper 10 that contact a wearer are shown oriented upwards in FIG. 2, and are shown facing the viewer in FIG. 3. FIG. 4 is a cross section of the diaper taken at line 4-4 in FIG. 3.

The diaper 10 generally may comprise a chassis 12 and an absorbent core 14 disposed in the chassis. The chassis 12 may comprise the main body of the diaper 10.

The chassis 12 may include a topsheet 18, which may be liquid pervious, and a backsheet 20, which may be liquid impervious. The absorbent core 14 may be encased between the topsheet 18 and the backsheet 20. The chassis 12 may also include side panels 22, elasticized barrier cuffs 24, and an elastic waist feature 26. The chassis 12 may also comprise a fastening system, which may include at least one fastening member 46 and at least one landing zone 48.

The barrier cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The crotch region 34 may include from 33.3% to 50% of the overall length of the diaper 10, and each of waist regions 30, 32 may correspondingly include from 25% to 33.3% of the overall length of the diaper 10.

The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 may also include such other features including front and rear ear panels, waist cap features, elastics and the like to provide better fit, containment and aesthetic characteristics. Such additional features are described in, e.g., U.S. Pat. No. 3,860,003 and U.S. Pat. No. 5,151,092.

In order to apply and keep diaper 10 in place about a wearer, the second waist region 32 may be attached by the fastening member 46 to the first waist region 30 to form leg opening(s) and an article waist. When fastened, the fastening system carries a tensile load around the article waist.

According to some examples, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, stretch laminates, activated stretch laminates, fiber reinforced plastics and the like, or combinations thereof. In some examples, the materials making up the fastening device may be flexible. In some examples, the fastening device may comprise cotton or cotton-like materials for additional softness or consumer perception of softness. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 may be fully or partially elasticized and/or may be foreshortened to create a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 20 may be joined with the topsheet 18. The backsheet 20 may serve prevent the exudates absorbed by the absorbent core 14 and contained within the diaper 10 from soiling other external articles that may contact the diaper 10, such as bed sheets and clothing. Referring to FIG. 2B, the backsheet 20 may be substantially impervious to liquids (e.g., urine) and comprise a laminate of a nonwoven 21 and a thin polymeric film 23 such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 20. Exemplary breathable materials may include materials such as woven webs, nonwoven webs, composite materials such as film-coated nonwoven webs, and microporous films such as manufactured by Mitsui Toatsu Co., of Japan under the designation ESPOIR and by EXXON Chemical Co., of Bay City, Tex., under the designation EXXAIRE. Suitable breathable composite materials comprising polymer blends are available from Clopay Corporation, Cincinnati, Ohio under the name HYTREL blend PI 8-3097. Other examples of such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

In some examples, the backsheet of the present invention may have a water vapor transmission rate (WVTR) of greater than about 2,000 g/24 h/m2, greater than about 3,000 g/24 h/m2, greater than about 5,000 g/24 h/m2, greater than about 6,000 g/24 h/m2, greater than about 7,000 g/24 h/m2, greater than about 8,000 g/24 h/m2, greater than about 9,000 g/24 h/m2, greater than about 10,000 g/24 h/m2, greater than about 11,000 g/24 h/m2, greater than about 12,000 g/24 h/m2, greater than about 15,000 g/24 h/m2, measured according to WSP 70.5 (08) at 37.8° C. and 600 Relative Humidity.

As noted, the nonwovens described herein may be used for the topsheet, backsheet outer cover, barrier cuffs or any other portion of the absorbent article comprising a nonwoven. To achieve desired softness attributes relating to loft and opacity, the nonwovens of the present invention may have a basis weight of greater than about 20 gsm, greater than about 22 gsm, greater than about 24 gsm, greater than about 26 gsm, greater than about 28 gsm, greater than about 30 gsm, greater than about 32 gsm.

The absorbent core generally may be disposed between the topsheet 18 and the backsheet 20. It may include one or more layers, such as a first absorbent layer 60 and a second absorbent layer 62.

The absorbent layers 60, 62 may include respective substrates 64, 72, an absorbent particulate polymer material 66, 74 disposed on substrates 64, 72, and a thermoplastic adhesive material 68, 76 disposed on and/or within the absorbent particulate polymer material 66, 74 and at least portions of the substrates 64, 72 as an adhesive for immobilizing the absorbent particulate polymer material 66, 74 on the substrates 64, 65.

The substrate 64 of the first absorbent layer 60 may be referred to as a dusting layer and has a first surface which faces the backsheet 20 and a second surface which faces the absorbent particulate polymer material 66. Likewise, the substrate 72 of the second absorbent layer 62 may be referred to as a core cover and has a first surface facing the topsheet 18 and a second surface facing the absorbent particulate polymer material 74.

The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

The substrates 64, 72 may be of one or more nonwoven materials, and may be liquid permeable.

As illustrated in FIG. 4, the absorbent particulate polymer material 66, 74 may be deposited on the respective substrates 64, 72 in clusters 90 of particles to form a grid pattern comprising land areas 94 and junction areas 96 between the land areas 94. Land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern contain little or no absorbent particulate polymer material 66 and 74. The land areas 94 and junction areas 96 can have a variety of shapes including, but not limited to, circular, oval, square, rectangular, triangular, and the like. First and second layers 60, 62 may be combined to form the absorbent core 14. Preferred absorbent articles and cores are described in U.S. application Ser. No. 12/141,122; U.S. Pat. Apps. Pub. Nos. 2004/0167486A1 and 2004/0162536; and PCT Pub. No. WO 2009/060384.

Combinations of features including but not limited to the following combinations are contemplated herein:

1. A nonwoven web material comprising fine fibers, the fine fibers comprising polyolefin and polyester.
2. The nonwoven web material of combination 1 comprising spunbond fibers, the spunbond fibers comprising polyolefin.
3. The nonwoven web material of combination 2, wherein the spunbond fibers further comprise polyester.
4. The nonwoven web material of combination 3, wherein the spunbond fibers are multicomponent fibers having a first component comprising predominately polyolefin and a second component comprising predominately polyester.
5. The nonwoven web material of combination 4, wherein the polyester is polylactic acid.
6. The nonwoven web material of either of combinations 4 or 5, wherein the polyolefin is polypropylene.
7. The nonwoven web material of any of combinations 4-6, wherein the multicomponent fibers are bicomponent fibers having a sheath-core configuration, with a sheath component and a core component.

8. The nonwoven web material of combination 7, wherein the sheath component is the first component and the core component is the second component.
9. The nonwoven web material of any of combinations 2-8, wherein the spunbond fibers form a first layer of the nonwoven web material and the fine fibers form a second layer of the nonwoven web material.
10. The nonwoven web material of any of the preceding combinations wherein the fine fibers comprise polypropylene and polylactic acid recycled from scrap material cut from an earlier-manufactured nonwoven web material.
11. An absorbent article comprising a topsheet, a backsheet, and an absorbent core disposed between the topsheet and the backsheet, wherein the nonwoven web material of any of combinations 1-8 forms a component of the absorbent article.
12. The absorbent article of combination 11 wherein the nonwoven web material forms, or forms a subcomponent of, one or more of the topsheet, the backsheet, a structure enveloping the absorbent core, barrier cuffs or side panels.
13. A nonwoven web comprising fine fibers derived from recycled materials and made according to a method comprising the steps of:
   procuring scrap material comprising a scrap polylactic acid component;
   hydrolyzing the scrap polylactic acid component to reduce its viscosity; blending the hydrolyzed scrap polylactic acid with a polyolefin resin to form a resin blend;
   melt-spinning the resin blend to form fine fibers and directing the fine fibers toward, and accumulating the fine fibers on, a moving surface.
14. A nonwoven web formed at least in part of fibers comprising polylactic acid obtained from recycled scrap, which has been hydrolyzed.
15. The nonwoven web of Combination 14 wherein the fibers are fine fibers.
16. The nonwoven web of either of Combinations 14 or 15 further comprising multicomponent spunbond fibers having a first component and a second component, wherein the first component comprises polylactic acid and the second component comprises polypropylene.
17. The nonwoven web of Combination 16 wherein the multicomponent spunbond fibers have a core/sheath configuration wherein a core section is the first component and a sheath section is the second component.
18. The nonwoven web of Combination 16, wherein the hydrolyzed polylactic acid is blended into at least one of the first and second components.
19. The nonwoven web of Combination 17 wherein the hydrolyzed polylactic acid is blended into at least one of the core or sheath sections.
20. The nonwoven web of any of the preceding combinations having at least a layer of spunbond fibers and a layer of fine fibers.
21. The nonwoven web of Combination 20 wherein the fine fiber layer is formed of fine fibers comprising hydrolyzed polylactic acid obtained from recycled scrap.

All patents and patent applications (including any patents which issue thereon) referred to herein are hereby incorporated by reference to the extent that it is consistent herewith.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web material comprising monocomponent fine fibers spun from a blend of resins including polypropylene and hydrolyzed polyester obtained from recycled scrap material comprising the polyester and a polyolefin.
2. The nonwoven web material of claim 1 comprising spunbond fibers, the spunbond fibers comprising polyolefin.
3. The nonwoven web material of claim 2, wherein the spunbond fibers further comprise polyester.
4. The nonwoven web material of claim 3, wherein the spunbond fibers are multicomponent fibers having a first component comprising predominately polyolefin and a second component comprising predominately polyester.
5. The nonwoven web material of claim 4, wherein the polyester is polylactic acid.
6. The nonwoven web material of claim 4, wherein the polyolefin is polypropylene.
7. The nonwoven web material of claim 4, wherein the multicomponent fibers are bicomponent fibers having a sheath-core configuration, with a sheath component and a core component.
8. The nonwoven web material of claim 7, wherein the sheath component is the first component and the core component is the second component.
9. The nonwoven web material of claim 2, wherein the spunbond fibers form a first layer of the nonwoven web material and the fine fibers form a second layer of the nonwoven web material.
10. The nonwoven web material of claim 1 wherein the polyester comprises polylactic acid and the scrap material is cut from an earlier-manufactured nonwoven web material.
11. An absorbent article comprising a topsheet, a backsheet, and an absorbent core disposed between the topsheet and the backsheet, wherein the nonwoven web material of claim 1 forms a component of the absorbent article.
12. The absorbent article of claim 11 wherein the nonwoven web material forms, or forms a subcomponent of, one or more of the topsheet, the backsheet, a structure enveloping the absorbent core, barrier cuffs or side panels.
13. A nonwoven web comprising fine fibers derived from recycled materials and made according to a method comprising the steps of:
   procuring scrap material comprising a scrap polylactic acid component and a scrap polyolefin component;
   hydrolyzing the scrap polylactic acid component to reduce its viscosity;
   blending the hydrolyzed scrap polylactic acid with a polypropylene resin to form a resin blend;
   melt-spinning the resin blend to form monocomponent fine fibers and directing the fine fibers toward, and accumulating the fine fibers on, a moving surface.

14. A nonwoven web formed at least in part of fibers comprising polylactic acid obtained from recycled scrap comprising the polylactic acid and a polyolefin, wherein the polylactic acid has been hydrolyzed.

15. The nonwoven web of claim 14 wherein the fibers are fine fibers.

16. The nonwoven web of claim 14 further comprising multicomponent spunbond fibers having a first component and a second component, wherein the first component comprises polylactic acid and the second component comprises polypropylene.

17. The nonwoven web of claim 16, wherein the hydrolyzed polylactic acid is blended into at least one of the first and second components.

18. The nonwoven web of claim 16 wherein the multicomponent spunbond fibers have a core/sheath configuration wherein a core section is the first component and a sheath section is the second component.

19. The nonwoven web of claim 18 wherein the hydrolyzed polylactic acid is blended into at least one of the core or sheath sections.

20. The nonwoven web of claim 14 having at least a layer of spunbond fibers and a layer of fine fibers.

21. The nonwoven web of claim 20 wherein the fine fiber layer is formed of fine fibers comprising hydrolyzed polylactic acid obtained from the recycled scrap.

* * * * *